(12) United States Patent
Wang et al.

(10) Patent No.: US 9,750,031 B2
(45) Date of Patent: Aug. 29, 2017

(54) COORDINATOR SWITCHING METHOD FOR MEDICAL BODY AREA NETWORKS

(71) Applicant: KONINKLIJKE PHILIPS N.V., Eindhoven (NL)

(72) Inventors: Dong Wang, Scarsdale, NY (US); David Hillary Evans, Crawley (GB)

(73) Assignee: Koninklijke Philips N.V., Eindhoven (NL)

( * ) Notice: Subject to any disclaimer, the term of this patent is extended or adjusted under 35 U.S.C. 154(b) by 131 days.

(21) Appl. No.: 14/419,249

(22) PCT Filed: Aug. 9, 2013

(86) PCT No.: PCT/IB2013/056520
§ 371 (c)(1),
(2) Date: Feb. 3, 2015

(87) PCT Pub. No.: WO2014/027288
PCT Pub. Date: Feb. 20, 2014

(65) Prior Publication Data
US 2015/0215925 A1    Jul. 30, 2015

Related U.S. Application Data

(60) Provisional application No. 61/683,858, filed on Aug. 16, 2012, provisional application No. 61/714,248, filed on Oct. 16, 2012.

(51) Int. Cl.
*H04W 72/04* (2009.01)
*A61B 5/00* (2006.01)
*H04W 84/18* (2009.01)

(52) U.S. Cl.
CPC ......... *H04W 72/048* (2013.01); *A61B 5/0024* (2013.01); *H04W 84/18* (2013.01)

(58) Field of Classification Search
CPC .................................................. H04W 72/048
See application file for complete search history.

(56) References Cited

U.S. PATENT DOCUMENTS 7,508,811 B2    3/2009    Shao et al.
8,045,534 B2    10/2011   Kwak et al.
(Continued)

FOREIGN PATENT DOCUMENTS

CN    102341034 A    2/2012
CN    102406500 A    4/2012
(Continued)

OTHER PUBLICATIONS

IEEE Standard for Local and Metropolitan Area Networks; Part 15.4: Low-Rate Wireless Personal Area Networks (LR-WPANs); 2012; Draft IEEE P802.15.4; pp. 1-53.

*Primary Examiner* — Brian D Nguyen
*Assistant Examiner* — Toan Nguyen (57) ABSTRACT

A coordinator switching method and corresponding apparatus (20) are provided. One or more candidate coordinators (64) to replace a coordinator (20) of a medical body area network (MBAN) (22) are identified. The coordinator (20) is associated with one or more devices (16, 18) of the MBAN (22). One of the identified candidate coordinators (64) is selected as a destination coordinator. The destination coordinator (64) is requested to replace the coordinator (20) and allocate resources for the devices (16, 18). Acceptance of the request and data identifying the allocated resources for the devices (16, 18) is received from the destination coordinator (64). The devices (16, 18) are instructed to associate with the destination coordinator (64) using the allocated resources.

18 Claims, 6 Drawing Sheets

(56) References Cited

U.S. PATENT DOCUMENTS

| | | | |
|---|---|---|---|
| 2005/0237979 A1 | 10/2005 | Kim et al. | |
| 2009/0023391 A1 | 1/2009 | Falck | |
| 2011/0007672 A1* | 1/2011 | Park | H04W 16/14 370/280 |
| 2011/0149759 A1 | 6/2011 | Jollota | |
| 2012/0051314 A1 | 3/2012 | Goyal et al. | |
| 2012/0089370 A1* | 4/2012 | Chebbo | A61B 5/0002 702/188 |
| 2012/0092155 A1 | 4/2012 | Abedi | |
| 2012/0106397 A1 | 5/2012 | Abedi | |
| 2012/0119902 A1* | 5/2012 | Patro | H04L 12/12 340/502 |
| 2012/0242501 A1* | 9/2012 | Tran | A61B 5/0024 340/870.02 |
| 2013/0010595 A1* | 1/2013 | Park | H04W 72/1252 370/231 |

FOREIGN PATENT DOCUMENTS

| | | |
|---|---|---|
| KR | 20110001843 A | 1/2011 |
| WO | 2008141719 A1 | 11/2008 |
| WO | 2010126342 A2 | 11/2010 |
| WO | 2011131723 A1 | 10/2011 |
| WO | 2013111965 A1 | 8/2013 |

* cited by examiner

| MHR FIELDS | COMMAND FRAME IDENTIFIER | NUMBER OF DEVICES | APPLICATION SPECIFIC INFORMATION |
|---|---|---|---|
| OCTETS: VARIABLE | 1 | 1 | VARIABLE |

FIG. 4

| MHR FIELDS | COMMAND FRAME IDENTIFIER |
|---|---|
| OCTETS: VARIABLE | 1 |

FIG. 5

| OCTETS: VARIABLE | 1 | 1 | 1 | 9*M | | | | |
|---|---|---|---|---|---|---|---|---|
| | | | | 8 | 1 | ... | 8 | 1 |
| MHR FIELDS | COMMAND FRAME IDENTIFIER | TOTAL NUMBER OF DEVICES (N) | REQUEST COMMAND SEQUENCE NUMBER | EXTENDED ADDRESS OF DEVICE 1 | CAPABILITY INFORMATION OF DEVICE 1 | ... | EXTENDED ADDRESS OF DEVICE M | CAPABILITY INFORMATION OF DEVICE M |

| MHR FIELDS | COMMAND FRAME IDENTIFIER | SWITCH STATUS | RESPOND COMMAND SEQUENCE NUMBER | SHORT ADDRESS OF DEVICE 1 | SHORT ADDRESS OF DEVICE 2 | ... | SHORT ADDRESS OF DEVICE M |
|---|---|---|---|---|---|---|---|
| OCTETS: VARIABLE | 1 | 1 | 0/1 | 2 | 2 | ... | 2 |
| | | | | | 2*M | | |

FIG. 8

| MHR FIELDS | COMMAND FRAME IDENTIFIER | NEW PAN ID | NEW PAN COORDINATOR SHORT ADDRESS | NEW PAN COORDINATOR EXTENDED ADDRESS | LOGICAL CHANNEL | CHANNEL PAGE | SHORT ADDRESS | SWITCH TIME |
|---|---|---|---|---|---|---|---|---|
| OCTETS: VARIABLE | 1 | 1 | 2 | 8 | 1 | 1 | 2 | 0/2 |

COORDINATOR SWITCHING METHOD FOR MEDICAL BODY AREA NETWORKS

CROSS REFERENCE TO RELATED APPLICATIONS

This application is a national filing of PCT application Serial No. PCT/IB2013/056520 filed Aug. 9, 2013, published as WO 2014/027277 A1 on Feb. 20, 2014, which claims the benefit of U.S. provisional application Ser. No. 61/683,848 filed Aug. 16, 2012, and U.S. provisional application Ser. No. 61/714,248 filed Oct. 16, 2012, both of which are incorporated herein by reference.

FIELD OF THE INVENTION

The present application relates generally to wireless communication. It finds particular application in conjunction with medical body area networks (MBANs) and will be described with particular reference thereto. However, it is to be understood that it also finds application in other usage scenarios and is not necessarily limited to the aforementioned application.

There is a general trend in the healthcare industry towards expanding care services, such as patient monitoring, to general wards and even beyond the physical hospital boundaries. Medical body area networks (MBANs) are one of the key enabling technologies for ubiquitous monitoring services. An MBAN is a wireless network of sensors around a patient used for monitoring a patient's physiological data. The clinical benefits of MBANs include: extension of monitoring into care areas that are currently unmonitored; improved healthcare workflow efficiency, safety and clinical outcome; patient mobility, comfort, and infection control; monitoring flexibility and scalability; and reduced overall monitoring costs. This is not intended to be an exhaustive list of benefits.

Figure 1:
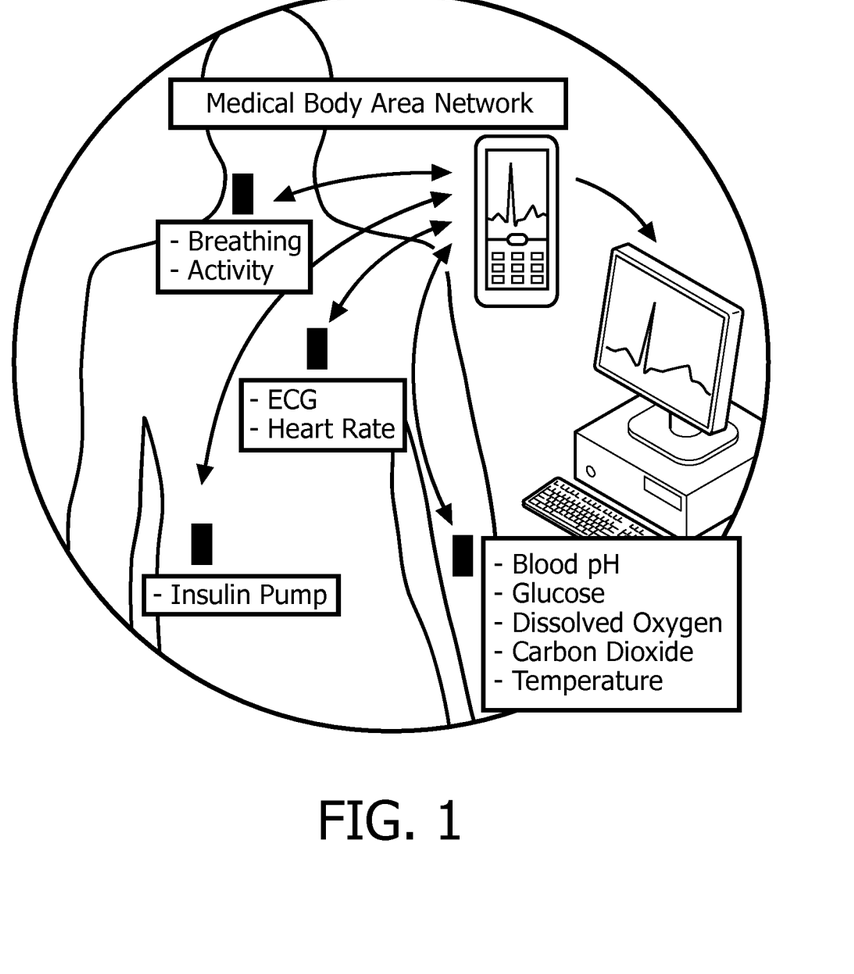
FIG. 1 illustrates a medical body area network (MBAN) system.

With reference to FIG. 1, a typical MBAN system includes several tiny sensor devices placed on a patient's body to capture physiological data of the patient, such as heart rate and electriocardiogram (ECG) signals. The captured data is forwarded to a hub device (i.e., a coordinator) through a short-range and low-power MBAN. The hub device could be a local bedside monitoring device, a cell phone, a set-top-box, or other wireless device and usually has a connection to a backhaul network (e.g., a cellular network, a local area network (LAN), etc.), through which the collected data is further transferred to a remote patient monitoring system. The remote patient monitoring system is responsible for analyzing patients' physiological data and provides monitoring, diagnosing or treating services in real time.

Currently, the Institute of Electrical and Electronics Engineers (IEEE) is developing wireless communication standards for MBAN applications. One example is the IEEE 802.15.4j standard in which physical (PHY)/media access control (MAC) layer enhancement features are under development to extend widely used IEEE 802.15.4 radios to better serve MBAN applications. Another example is the IEEE 802.15.6 standard, which provides a PHY/MAC solution for medical/non-medical body area network applications.

Coordinator switching can be a useful feature to provide continuous monitoring services to patients even during transport with no or minimal caregiver intervention. One use scenario is when a patient's operation is finished and the patient needs to be transported from the operation room (OR) to a step-down unit. To provide monitoring services during transport, a portable monitor device (e.g., a telemetry monitor device) will replace the bedside monitor device used in the OR as a coordinator. The portable monitor device will receive patient physiological data from the sensor devices attached to the patient and continue monitoring services. Another use scenario is when a patient moves back to their room after medical exams/tests. A bedside monitor device in the patient's room will replace a portable monitor device as the coordinator. Usually, a bedside monitor device has mains power, a bigger display screen, a more powerful CPU, and a wired network connection. Further, it is usually a better choice to provide monitoring services in a patient room.

In those scenarios, and others, coordinator switching is a challenge. A coordinator switching method is needed in those scenarios to transfer the coordinator role between a bedside monitor and a portable monitor without disturbing MBAN monitoring services. Currently, caregivers (e.g., nurses) need to perform coordinator switching by manually disconnecting cables attached to the sensor devices from the current monitor device and reconnecting the cables to a new monitor device. In some cases, they may need to replace the sensor devices too due to cable interface incompatibility. This can decrease workflow efficiency and disturb monitoring services. MBAN makes more automatic and context aware coordinator switching possible. Therefore, a new coordinator switching method that requires minimal or no caregiver intervention is needed.

The present application provides a new and improved method which overcomes the above-referenced problems and others.

SUMMARY

According to one aspect, a coordinator of a medical body area network (MBAN) associated with one or more devices of the MBAN is provided. The coordinator includes a controller configured to identify one or more candidate coordinators to replace the coordinator, select one of the identified candidate coordinators as a destination coordinator, request the destination coordinator to replace the coordinator and allocate resources for the devices, receive acceptance of the request and data identifying the allocated resources for the devices from the destination coordinator, and instruct the devices to associate with the destination coordinator using the allocated resources.

According to another aspect, a coordinator switching method is provided. One or more candidate coordinators to replace a coordinator of a medical body area network (MBAN) are identified. The coordinator is associated with one or more devices of the MBAN. One of the identified candidate coordinators is selected as a destination coordinator. The destination coordinator is requested to replace the coordinator and allocate resources for the devices. Acceptance of the request and data identifying the allocated resources for the devices are received from the destination coordinator. The devices are instructed to associate with the destination coordinator using the allocated resources.

According to another aspect, a candidate coordinator includes a controller. The controller is configured to receive a coordinator switching inquiry from a controller of a medical body area network (MBAN). The coordinator is associated with one or more devices of the MBAN. The controller is further configured to transmit a response to the coordinator switching inquiry indicating a willingness to replace the coordinator to the coordinator, receive a request to replace the coordinator, allocate resources for the devices, transmit a response accepting the request to the coordinator, and receive data from the devices using the allocated resources. The request identifies the devices, and the response includes data identifying the allocated resources for the devices.

One advantage resides in improved coordinator switching.

Another advantage resides in no or minimal caregiver intervention.

Another advantage resides in continuous monitoring.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

As described hereafter, a coordinator switching method is proposed for medical body area networks (MBANs). Media access control (MAC) layer procedures and commands are defined for the Institute of Electrical and Electronics Engineers (IEEE) 802.15.4j standard as an example. However, the proposed scheme can also be implemented for other MBAN systems, such as IEEE 802.15.6 based systems, and within other other high layer protocols.

Figure 2:
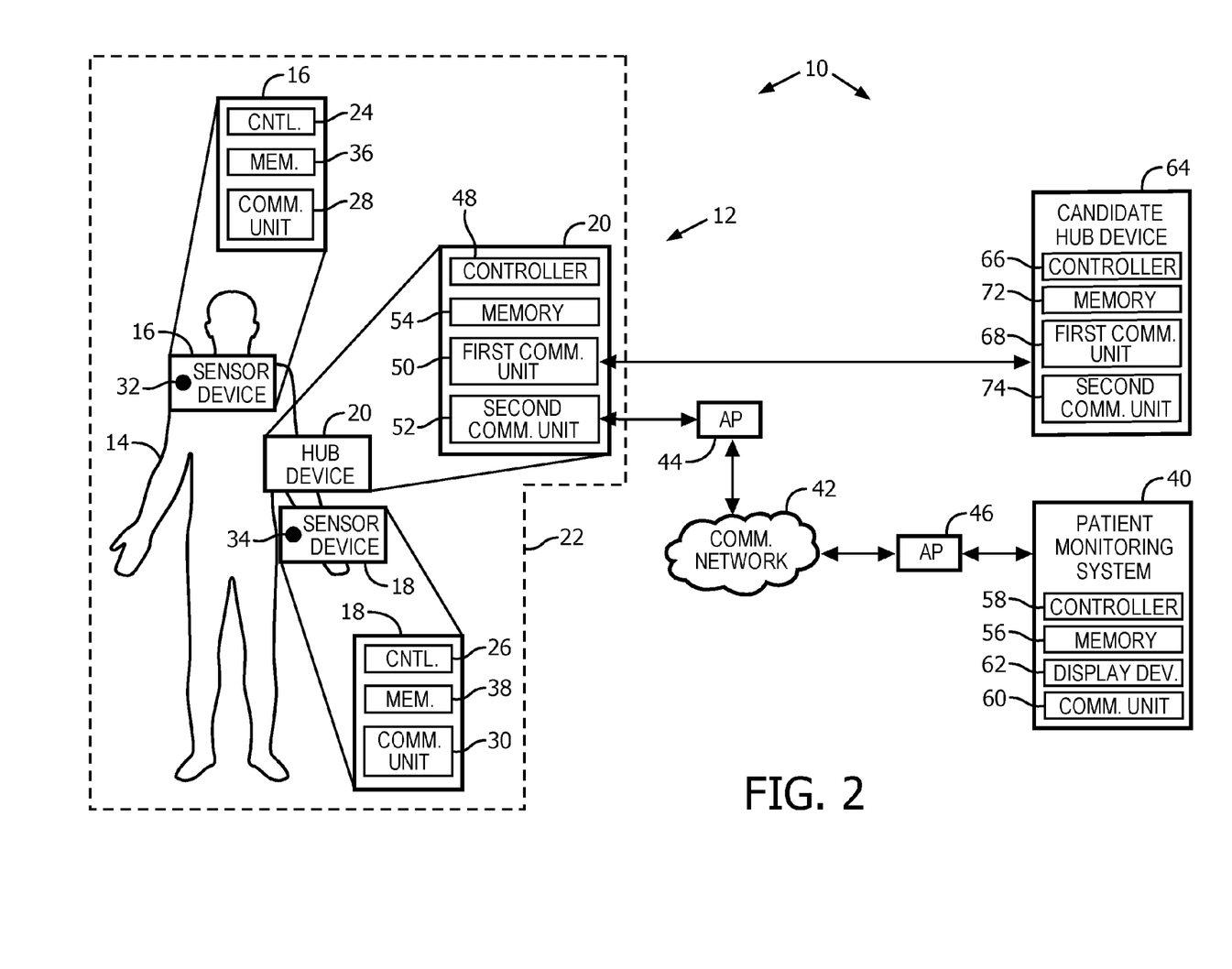
FIG. 2 illustrates a block diagram of a medical system.

With reference to FIG. 2, a medical system 10 includes a medical body area network (MBAN) system 12. The MBAN system 12 is associated with a patient 14 and is deployed to capture patient physiological data of the patient 14. Further, the MBAN system 12 includes one or more sensor devices 16, 18 and a hub device 20 (i.e., originator coordinator) communicating over an MBAN 22 of the MBAN system 12. The MBAN 22 is a network (e.g., a short-range wireless network) employing a communication standard (e.g., IEEE 802.15.6 and IEEE 802.15.4j) augmented to perform the coordinator switching method discussed hereafter.

The sensor devices 16, 18 capture physiological data of the patient 14, such as heart rate, respiration rate, blood pressure, ECG signals, and so forth, in real-time and forward the data to the hub device 20 over the MBAN 22. The sensor devices 16, 18 are typically disposed on the exterior of the patient 14. For example, the sensor devices 16, 18 can be on-body and/or wearable sensor devices. However, the sensor devices 16, 18 can additionally or alternatively disposed in the patient 14 and/or proximate to the patient 14.

Each of the sensor devices 16, 18 includes a controller 24, 26, a communication unit 28, 30, and at least one sensor 32, 34 for measuring at least one physiological parameter of the patient 14. The controller 24, 26 captures the physiological data using the at least one sensor 32, 34 and transmits the captured physiological data to the hub device 20 using the communication unit 28, 30. The controller 24, 26 can immediately transmit the captured physiological data upon receiving it. Alternatively, the controller 24, 26 can buffer or otherwise store the captured physiological data in a memory 36, 38 of the sensor device 16, 18 and only transmit the buffered physiological data when the amount exceeds a threshold. The communication unit 28, 30 communicates with the hub device 20 over the MBAN 22.

The hub device 20 is responsible for one or more of: 1) collecting physiological data from the sensor devices 16, 18; 2) managing the sensor devices 16, 18 (e.g., acting as a personal area network (PAN) coordinator); and 3) transferring collected physiological data to a patient monitoring system 40 of the medical system 10 over a second communication network 42, such as a wired Ethernet, Wi-Fi, or 3G/4G cellular network. The second communication network 42 is typically long-range compared to the MBAN 22. When the second communication network 42 includes a wireless interface, it includes one or more access points 44, 46 for wireless communication. The hub device 20 is typically disposed proximate to the patient 14. Further, the hub device 20 is typically one of a local bedside monitoring unit, a cell phone, a set-top-box, or other wireless device.

The hub device 20 includes a controller 48 and a first communication unit 50. The first communication unit 50 communicates with the sensor devices 16, 18 using the MBAN 22. The controller 48 can act as the PAN coordinator for the MBAN 22 using the first communication unit 50. In doing so, the controller 48 controls the first communication unit 50 to set up the MBAN 22, associate/disassociate the sensor device 16, 18 with the MBAN 22, and so on. The controller 48 can further receive the captured physiological data from the sensor devices 16, 18 using the first communication unit 50.

The controller 48 can also transmit the received physiological data to the patient monitoring system 40 using a second communication unit 52 of the hub device 20. The controller 48 can immediately transmit the received physiological data to the patient monitoring system 40 upon receiving it. Alternatively, the controller 48 can buffer or otherwise store the received physiological data in a memory 54 of the hub device 20 and only transmit the buffered physiological data when the amount exceeds a threshold. The second communication unit 52 communicates with the patient monitoring system 40 using the second communication network 42.

The patient monitoring system 40 facilitates monitoring of the patients for degradation using physiological data received from the MBAN system 12, specifically, the hub device 20 of the MBAN system 12, over the second communication network 42. The patient monitoring system 40 one or more of: 1) receives patient data forwarded by the hub devices 20; 2) analyzes physiological data and stores physiological data in a memory 56 of the patient monitoring system 40; 3) provides monitoring, diagnosing or treating services in real time; and 4) so on. The patient monitoring system 40 is typically remote from the MBAN systems 12.

The patient monitoring system 40 includes a controller 58 and a communication unit 60. The communication unit 60 allows the controller 58 to communicate with devices over the second communication network 42. For example, the communication unit 60 allows the controller 58 to communicate with the MBAN system 12, specifically the hub device 20 of the MBAN system 12, over the second communication network 42.

The controller 58 can receive physiological data from the hub devices 20. Further, using the received physiological data, the controller 58 can monitor and/or track patient health conditions, and issue alarms based thereon. The controller 58 can determine whether to issue an alarm by matching the received physiological data to alarm criteria. For example, an alarm may be issued if at least one physiological parameters exceeds thresholds. The alarm criteria can take in to account the present values of physiological parameters, as well as trends of physiological parameters. The controller 58 can also generate early warnings based on long-term patient health condition prediction. Further, the controller 58 can display the received physiological data on a display device 62 of the patient monitoring system 40 and/or store the received physiological data in the memory 56 of the patient monitoring system 40.

The medical system 10 further includes one or more candidate hub devices 64 (i.e., candidate coordinators). Each of the candidate hub devices 64 is a candidate for replacing the hub device 20 in the MBAN system 12. The candidate hub device 64, when used in place of the hub device 20, takes on the roles of the hub device 20. Namely, the candidate hub device 64 would be responsible for one or more of: 1) collecting physiological data from the sensor devices 16, 18; 2) managing the sensor devices 16, 18 (e.g., acting as a personal area network (PAN) coordinator); and 3) transferring collected physiological data to the patient monitoring system 40 over the second communication network 42. The candidate hub device 64 is typically disposed proximate to the patient 14, and is typically one of a local bedside monitoring unit, a cell phone, a set-top-box, or other wireless device.

The candidate hub device 64 includes a controller 66 and a first communication unit 68. The first communication unit 68 allows communication with the sensor devices 16, 18 using the MBAN 22. The controller 66 can act as the PAN coordinator for the MBAN 22 using the first communication unit 68. The controller 66 can also coordinate with the hub device 20 to replace the hub device 20 as coordinator using the first communication unit 68. The controller 66 can further receive the captured physiological data from the sensor devices 16, 18 using the first communication unit 68.

The controller 66 can also transmit the received physiological data to the patient monitoring system 40 using a second communication unit 70 (e.g., a long range communication unit) of the candidate hub device 64. The controller 66 can immediately transmit the received physiological data to the patient monitoring system 40 upon receiving it. Alternatively, the controller 66 can buffer or otherwise store the received physiological data in a memory 72 of the candidate hub device 64 and only transmit the buffered physiological data when the amount exceeds a threshold. The second communication unit 70 communicates with the patient monitoring system 40 using the second communication network 42.

In another embodiment, the sensor devices 16, 18 communicate, such as with body coupled communications, with a patient-carried unit, which in turn communicates the data from all of the sensor devices 16, 18 to the hub device 20.

Figure 3:
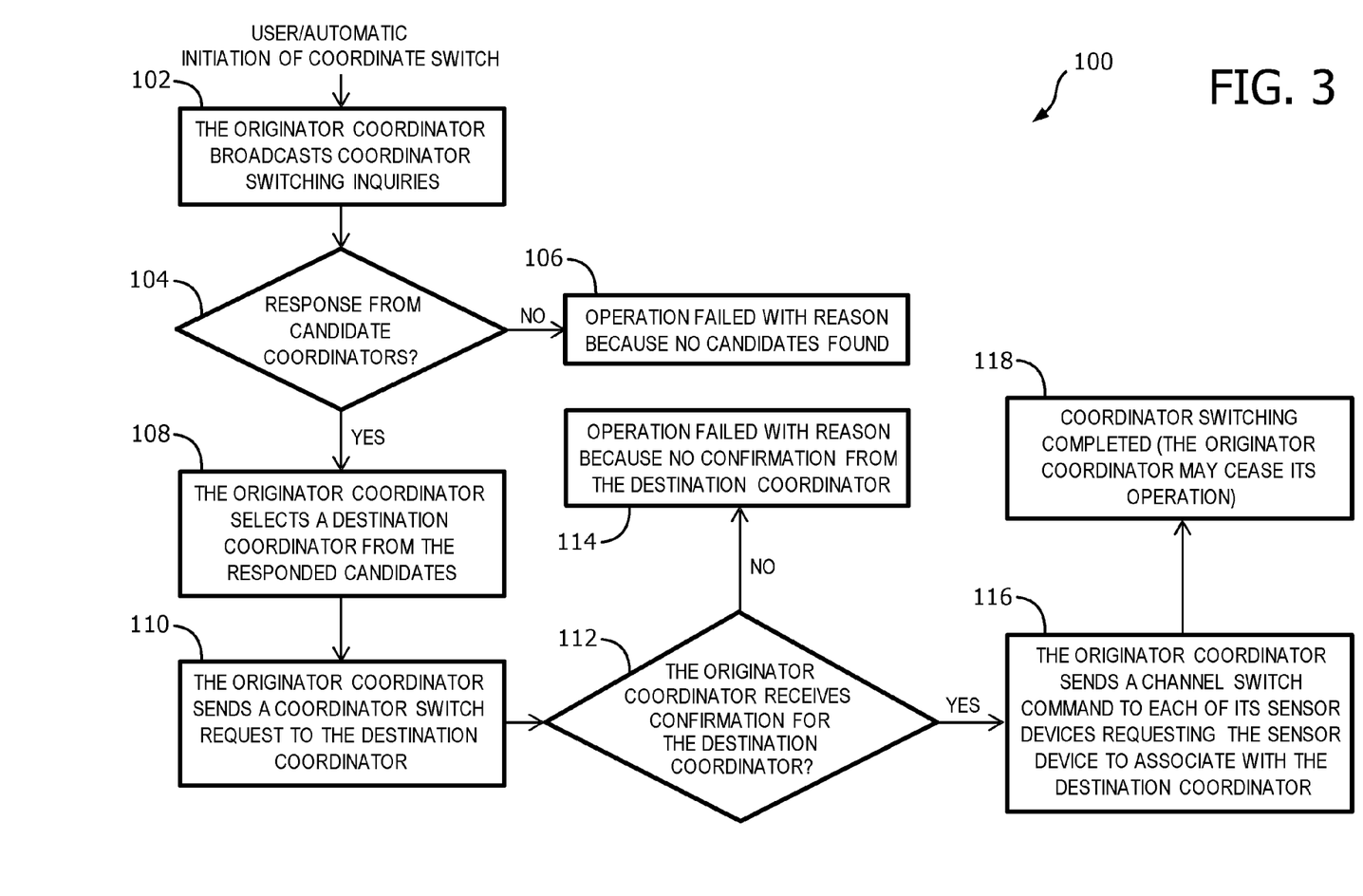
FIG. 3 illustrates a coordinator switching procedure diagram.

With reference to FIG. 3, a proposed coordinator switching procedure 100 for replacing the hub device 20 (i.e., originator coordinator) with one of the candidate hub devices 64 (i.e., candidate coordinators) is shown. The communication units 28, 30, 50, 68, and/or the controllers 24, 26, 48, 66, of the sensor devices 16, 18, the hub device 20, and the candidate hub devices 64 suitably implement the proposed coordinator switching procedures. For example, the communication units 28, 30, 50, 68 can implement the proposed switching scheme in hardware. As another example, the controllers 24, 26, 48, 66 can implement the proposed switching scheme in software stored on memories of the controllers 24, 26, 48, 66 which is executed by processors of the controllers 24, 26, 48, 66. As another example, a combination of hardware and software can be employed.

The coordinator switching operation can be initiated by a caregiver, for example, by pushing a button on the originator coordinator 20, or by the originator coordinator 20 itself triggered by a context change, such as a change which limits the ability of the originator coordinator 20 to maintain its current level of functionality (e.g., low battery warning, network connection issues, etc.). First, the originator coordinator 20 switches to each channel in its candidate channel list (i.e., a list of channels within which it is enabled to operate) and broadcasts 102 a coordinator switching inquiry on that channel using a coordinator switch inquiry command indicating the number of the sensor devices that it wishes to switch and/or other application specific information.

Figure 4:
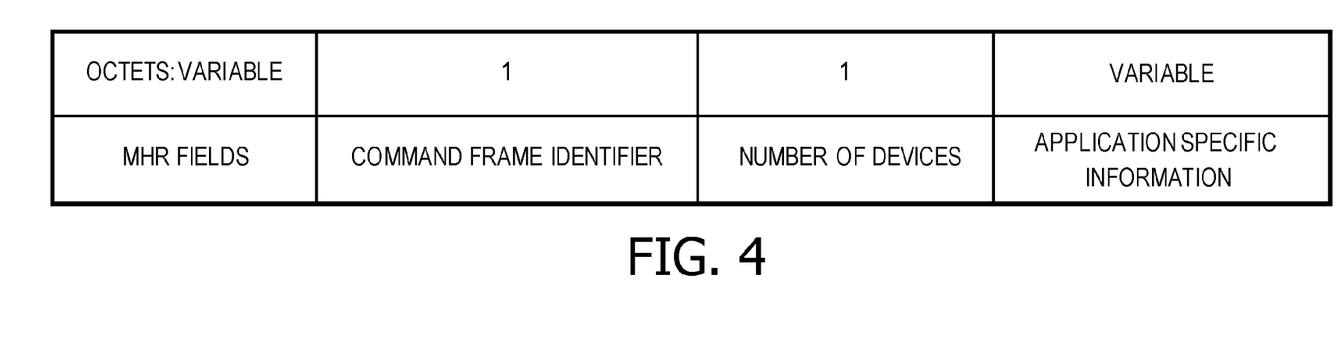
FIG. 4 illustrates a coordinator switch inquiry command format.

For the IEEE 802.15.4j standard, a proposed MAC frame format for the coordinator switch inquiry command is shown in FIG. 4. The MHR (i.e., MAC header) fields follow the IEEE 802.15.4j structure. The MHR fields (not illustrated in detail) include a Destination Addressing Mode field, a Destination PAN Identifier field, a Destination Address field, a Source Addressing Mode field, a Source PAN ID field and a Source Address field. The short addressing mode is used for the Destination Addressing Mode field, and the Destination PAN Identifier field and the Destination Address field are set to the broadcast PAN identifier and the broadcast short address, respectively. The Source Addressing Mode field is set to indicate extended addressing. The Source PAN ID field and the Source Address contain the PAN ID and the extended address, respectively, of the originator coordinator 20.

The Number of Devices field is used to indicate the total number of the sensor devices 16, 18 that are associated with the originator coordinator 20 and that will be switched. The Application Specific Information field is optional and to provide extra information, such as an identifier (ID) of the patient 14 or a service ID of a patient monitoring service running on the current MBAN 22. The extra information can help a candidate coordinator 64 evaluate whether it has sufficient resources to support the services running on the originator coordinator 20. Further, the extra information can help a candidate coordinator 64 do a security check and/or perform authentication.

Referring back to FIG. 3, once a candidate coordinator 64 receives a coordinator switch inquiry command, it will check if the inquiry is an authentic inquiry, for example, using the application specific information (e.g., Patient ID) and the source PAN identifier and/or source address. If it is a valid inquiry, a candidate coordinator 64 can check whether it has sufficient resource and/or capabilities to support the requested coordinator switch operation. If a candidate coordinator 64 determines that it can and is willing to support the coordinator switch operation, it will send a coordinator switch inquiry response command to the originator coordinator 20 to indicate its willingness to support such coordinator switch. Otherwise, a candidate coordinator 64 drops the received inquiry command and does nothing.

Figure 5:
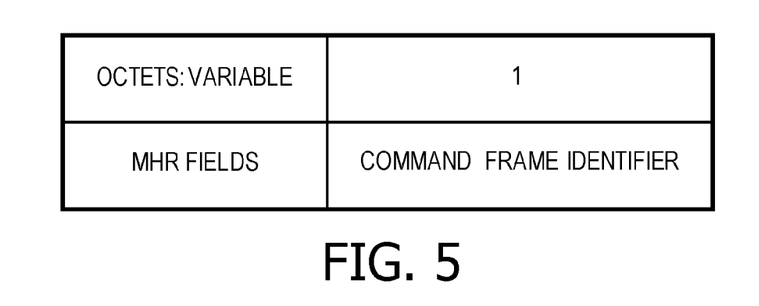
FIG. 5 illustrates a coordinator switch inquiry response command format.

For the IEEE 802.15.4j standard, a proposed MAC frame format for a proposed coordinator switch inquiry response command is shown in FIG. 5. The MHR fields follow the IEEE 802.15.4j structure. The Destination Addressing Mode and the Source Addressing Mode fields are each set to indicate extended addressing. The Destination PAN ID field and the Destination Address field contain the PAN ID and the extended address of the originator coordinator 20, respectively, while the Source PAN ID field and the Source Address contain the PAN ID and the extended address, respectively, of the candidate coordinator 64 that sends the current response command.

Referring back to FIG. 3, after sending a coordinator switch inquiry, the originator coordinator 20 switches to a receive mode and waits to receive inquiry responses from any candidate coordinators 64 for a predefined time period. The originator coordinator 20 records the received responses and then switches to a next channel to continue its inquiries. After scanning all channels, the originator coordinator 20 determines 104 whether any responses were received. If no response is received from any of the candidate coordinators 64, the originator coordinator 20 abandons 106 the coordinator switch operation and reports an "operation failure" message. Otherwise, the originator coordinator 20 selects 108 one of the responding candidate coordinators 64 as a destination coordinator. To facilitate the selection, the originator coordinator 20 may order and/or otherwise rank the candidate coordinators 64 that send responses to it.

Once the originator coordinator 20 selects a destination coordinator 64, it switches to the channel of the destination coordinator 64 and sends 110 one or more coordinator switch request commands to the destination coordinator 64 to request it to perform a coordinator switch operation. The coordinator switch commands include the necessary information for the destination coordinator 64 to determine whether it has sufficient resources to handle the sensor devices 16, 18 and to allocate resources (e.g., addresses) for the sensor devices 16, 18 if there are sufficient resources.

Figure 6:
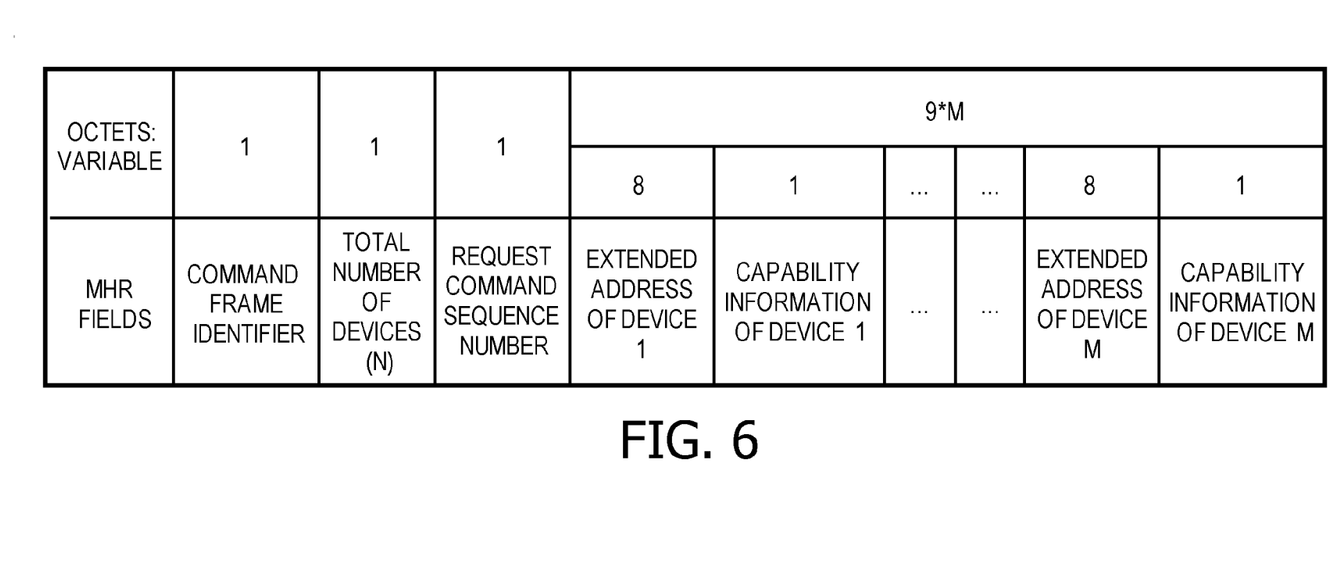
FIG. 6 illustrates a coordinator switch request command format.

For the IEEE 802.15.4j standard, a proposed MAC frame format for a proposed coordinator switch request command is shown in FIG. 6. The MHR fields follow the IEEE 802.15.4j structure. The Destination Addressing Mode and the Source Addressing Mode fields are each set to indicate extended addressing. The Source PAN ID field and the Source Address field contain the PAN ID and the extended address of the originator coordinator 20, respectively, while the Destination PAN ID field and the Destination Address contain the PAN ID and the extended address, respectively, of the destination coordinator 64. The Total Number of Devices (N) field indicates the number of sensor devices 16, 18 that the originator coordinator 20 plans to switch to the destination coordinator 64. This number should be no larger than the one indicated in the previous coordinator switch inquiry command.

In the coordinator switch request command, a Device Extended Address field and a Capability Information field are included for each sensor device 16, 18. Due to packet length limits (e.g., the maximum physical layer service data unit (PSDU) size is 127 octets), in each coordinator switch request command, at most 9 (i.e., M<=9) sensor devices' extended addresses and capability information are included. Therefore, if the total number of the sensor devices 16, 18 to be switched by the originator coordinator 20 is larger than 9 (i.e., N>9), then more than one coordinator switch request command is required to convey all the information (i.e., extended address and capability information) of the N sensor devices to the destination coordinator 64.

The Request Command Sequence Number field is used to track the command sequence. The first request command of each coordinator switching operation sets the field to "1" and increases sequentially for the following commands in the operation. If more than one request commands are needed, then a Frame Pending bit of the MHR fields is set to "1" for all but the last request command to indicate one or more request commands will follow and M=9 sensor devices' information is included, except for the last request command. For the last request command, the Frame Pending field is set to "0" to indicate it is the last request command and M is ((N−1) mod 9)+1, where mod is the modulo operator.

Also, for the request commands, the ACK Request bit of the MHR fields is set to "1". This prompts the destination coordinator 64 to immediately reply with an "ACK" once a request command is correctly received. The ACKs confirm with the originator coordinator 20 that the request commands are received correctly by the destination coordinator 64 and do not mean that the destination coordinator 64 accepts the switch request.

Referring back to FIG. 3, after receiving all the request commands for a coordinator switch operation, the destination coordinator 64 determines whether to accept the request or not, for example, based on its current resource status in a predefined period. After it makes the decision, the destination coordinator 64 will send one or more coordinator switch response commands to the originator coordinator 20 within a predefined time period to indicate its decision. If the destination coordinator 20 accepts the request, it will also allocate resources (e.g., addresses) for the sensor devices 16, 18 and include data identifying the allocated resources in the coordinator switch response command.

Figure 7:
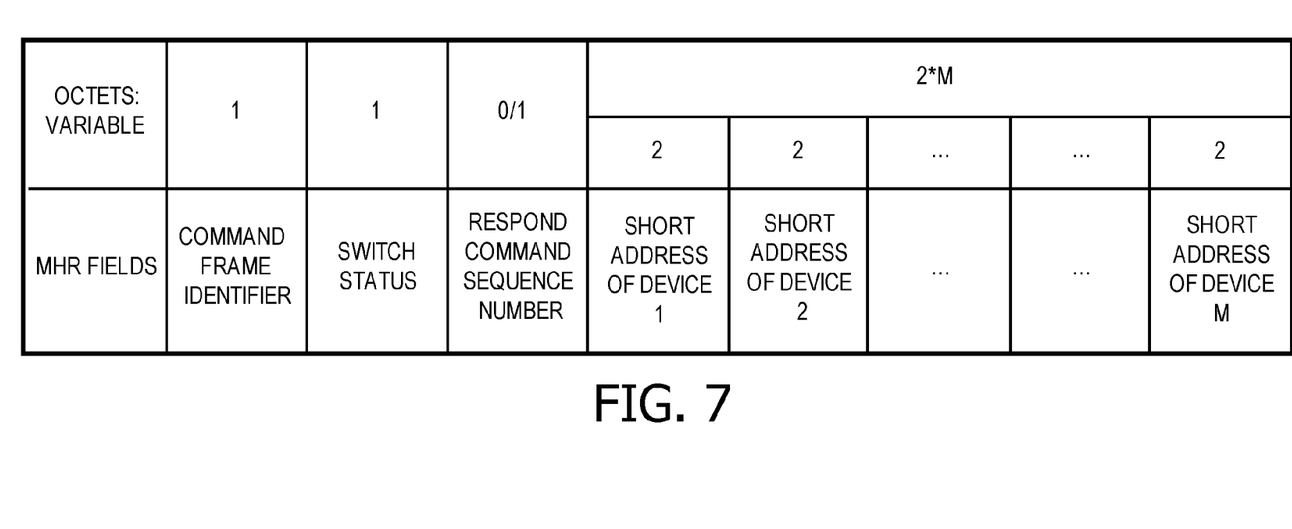
FIG. 7 illustrates a coordinator switch response command format.

For the IEEE 802.15.4j standard, a proposed MAC frame format for a proposed coordinator switch response command is shown in FIG. 7. The MHR fields follow the IEEE 802.15.4j structure. The Switch Status field is used to indicate whether the destination coordinator 64 accepts the coordinator switch request. If the destination coordinator 64 accepts the request and allows associating the requested number (N) of sensor devices 16, 18 to its PAN, this field contains the value of the Number of Devices field (N) in the received coordinator switch request command(s). Otherwise, if the destination coordinator 64 is not able to associate the requested number of devices to its PAN, this field contains "0x00".

If the destination coordinator 64 accepts the coordinator switch request, the Respond Command Sequence Number and Short Address fields are included. For each received coordinator switch request command, a corresponding coordinator switch response command is sent. The Respond Command Sequence Number field is set to "1" for the first response command in this operation and increases sequentially for the following response command(s). The response command with the Respond Command Sequence Number of S is to respond the request command with the Request Command Sequence Number of S.

The Short Address fields provide the allocated short addresses for the corresponding sensor devices 16, 18 indicated in the request commands. In other words, the Short Address field of Device i in the response command with sequence number of S is the allocated short address (allocated by the destination coordinator 64) for the sensor device 16, 18 with the ith extended address in the Sth switch request command. If more than one response commands are needed, then the Frame Pending bit of the Frame Control field of the MHR fields is set to "1" to indicate more response command(s) will follow and M=9 short device addresses are included, except for the last request command. For the last request command, the Frame Pending bit is set to "0" to indicate it is the last request command and M is ((N−1) mod 9)+1, where mod is the modulo operator.

Also, for the response commands, the ACK Request bits of the MHR fields are set to "1". Once the coordinator switch response command is correctly received, the originator coordinator 20 replies with an ACK immediately.

The Destination Addressing Mode field is set to indicate extended addressing, while the Source Addressing Mode field is set to indicate short addressing. The Source PAN ID field and the Source Address field contain the PAN ID and the short address of the destination coordinator 64, respectively, while the Destination PAN ID field and the Destination Address field contain the PAN ID and the extended address of the originator coordinator 20, respectively. In this way, the originator coordinator 20 can obtain the short address of the destination coordinator.

Referring back to FIG. 3, a determination 112 is made as to whether the originator coordinator 20 received confirmation for the destination coordinator 64. The originator coordinator 20 only receives confirmation when all of the request and/or response commands and ACKs are correctly received. If confirmation is not received, the coordinator switch operation is abandoned (e.g., release the reserved resource, such as the allocated short addresses) and treated as failed 114. If the originator coordinator 20 correctly receives all the coordinator switch response commands, it instructs its sensor devices 16, 18 to switch and associate to the destination coordinator 64 by sending 116 a channel switch command to each of its sensor devices 16, 18 to be switched to the destination coordinator 64. The channel switch command further includes the data identifying the resources allocated to the sensor device 16, 18.

Figure 8:
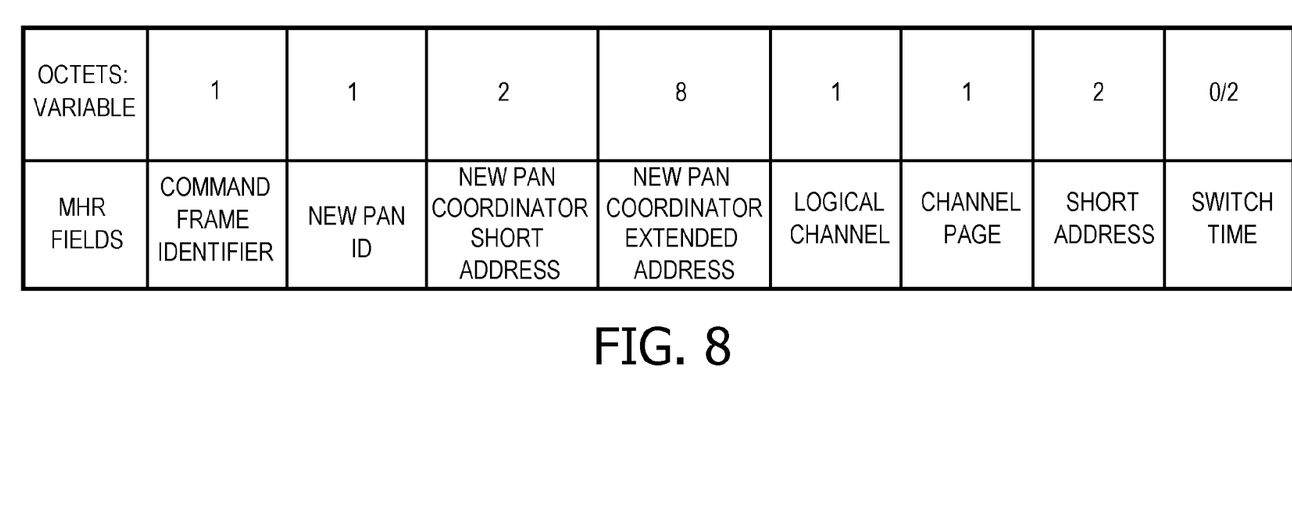
FIG. 8 illustrates a channel switch command format.

For the IEEE 802.15.4j standard, a proposed MAC frame format for a channel switch command is shown in FIG. 8. The MHR fields follow the IEEE 802.15.4j structure. In the beacon enabled mode, a channel switch command is sent to each of the sensor devices 16, 18 of the originator coordinator 20 via indirect data transfer (i.e., including an indication in the beacon to let the sensor device 16, 18 know there is pending data for it to retrieve). This will prompt the sensor device 16, 18 to initiate data transfer. In the non-beacon mode, a channel switch command is sent directly to each of the sensor device 16, 18 of the originator coordinator 20.

In the channel switch command, the PAN ID, short and extended addresses, and the logical channel and channel page of the destination coordinator 64 are provided to help a sensor device 16, 18 find the destination coordinator. An optional Switch Time field can be included to indicate when the sensor device 16, 18 should initiate the switch operation. If no such field is included, then the sensor device 16, 18 initiates the switch immediately after this communication (i.e., after finishing ACK transmission). The ACK Request bit of the MHR fields is set to "1". This prompts the sensor device 16, 18 to immediately reply with an ACK once correctly receiving a channel switch command.

When performing a switch, the sensor device 16, 18 switches to the channel that is specified by the Logical Channel and Channel Page fields and continues its communications with the destination coordinator 64 specified by New PAN ID, the New PAN Coordinator Short Address, and the New PAN Coordinator Extended Address field. The sensor device 16, 18 doesn't need to do a channel scan and an association procedure with the destination coordinator 64 since the destination coordinator 64 has already allocated a short address for the sensor device 16, 18 and recognizes the sensor device 16, 18 as one of its associated device. This can help reduce overhead.

Referring back to FIG. 3, once the originator coordinator 20 completes the communication of the channel switch command to a sensor device 16, 18 either successfully (i.e., received ACK) or unsuccessfully, it treats the sensor device 16, 18 as disassociated and removes it from its PAN. If a channel switch command is not correctly communicated to a sensor device 16, 18, the sensor device 16, 18 may identify itself as an orphan device and will start orphan device realignment procedure to join the PAN of the destination coordinator 64. Once the originator coordinator 20 disassociates all of the sensor devices 16, 18 coordinator switching is completed 118.

While the proposed scheme was described for IEEE 802.15.4j standard, it can also be implemented for other standards, such as IEEE 802.15.6. Further, while the proposed scheme was described as part of MAC protocol layer, it can be employed within other high layer protocols. The proposed scheme can be used for 802.15.4j based patient monitoring products. It can also provide a proprietary solution to extend current IEEE 802.15.4 and/or 802.15.6 based patient monitoring solutions to support flexible patient monitor selection for ambulatory patient monitoring applications.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory with processor executable instructions and at least one processor executing the processor executable instructions; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A coordinator of a medical body area network (MBAN) associated with one or more devices of the MBAN and comprising:
   a controller configured to:
   identify one or more candidate coordinators to replace the coordinator;
   transmit one or more switch inquiry requests for a candidate coordinator to replace the coordinator;
   receive one or more switch inquiry responses from the candidate coordinators for a predetermined time interval;

select one of the identified candidate coordinators as a destination coordinator;

request the selected destination coordinator to replace the coordinator and allocate resources for the devices identified in the request;

receive acceptance of the request and data identifying the allocated resources for the devices from the selected destination coordinator; and instruct the devices to associate with the selected destination coordinator using the allocated resources; and at least one of:

transmit a switch inquiry request for a candidate coordinator to replace the coordinator on each channel for which the coordinator is authorized to operate on; and receive the switch inquiry responses from the candidate coordinators on the channels for which the coordinator is authorized to operate on for a predetermined time interval; and the switch inquiry requests include data identifying the number of devices associated with the coordinator and authentication data which includes at least one of a patient identifier and a service identifier.

2. The coordinator according to claim 1, wherein the controller is further configured to:

identify the candidate coordinators to replace the coordinator in response to a change in the state of coordinator which limits the ability of the coordinator to maintain its current level of functionality.

3. The coordinator according to claim 1, wherein the controller is further configured to:

transmit a switch inquiry request for a candidate coordinator to replace the coordinator on each channel for which the coordinator is authorized to operate on; and, receive the switch inquiry responses from the candidate coordinators on the channels for which the coordinator is authorized to operate on for a predetermined time interval.

4. The coordinator according to claim 1, wherein the switch inquiry requests include data identifying the number of devices associated with the coordinator and authentication data which includes at least one of a patient identifier and a service identifier.

5. The coordinator according to claim 1, wherein the allocated resources are addresses for the devices which are identified in the request to replace the coordinator.

6. The coordinator according to claim 1, wherein the MBAN employs in the request and response message formats one of IEEE 802.15.4j and IEEE 802.15.6; and wherein the switch response message includes one or more messages with a short address of each allocated device.

7. The coordinator according to claim 1, wherein the resources needed for the destination coordinator to communicate with the devices are allocated before the devices associated with the destination coordinator; and wherein the request includes capability information for each device.

8. The coordinator according to claim 1, wherein the devices are sensor devices measuring physiological parameters of the patient identified in the switch inquiry request.

9. The coordinator according to claim 8, wherein the controller is further configured to:

receive physiological data of the measured physiological parameters from the sensor devices over the MBAN; and, relay the received physiological data to a patient monitoring system over a second communication network which analyzes the physiological data in real-time.

10. A coordinator switching method comprising:

identifying one or more candidate coordinators to replace a coordinator of a medical body area network (MBAN), the coordinator associated with one or more devices of the MBAN;

transmitting a switch inquiry request for one of the identified candidate coordinators to replace the coordinator on each channel for which the coordinator is authorized to operate on receiving the switch inquiry responses from at least one of the candidate coordinators on the channels for which the coordinator is authorized to operate on for a predetermined time interval;

selecting one of the identified candidate coordinators as a destination coordinator;

requesting the destination coordinator to replace the coordinator and allocate resources for the devices identified in the request;

receiving acceptance of the request and data identifying the allocated resources for the devices from the destination coordinator; and instructing the devices to associate with the destination coordinator using the allocated resources.

11. The coordinator switching method according to claim 10, further including:

identifying the candidate coordinators to replace the coordinator in response to a change in the state of coordinator which limits the ability of the coordinator to maintain its current level of functionality.

12. The coordinator switching method according to claim 10, wherein the devices are sensor devices measuring physiological parameters of a patient which are identified in the request to replace the coordinator.

13. The coordinator switching method according to claim 12, further including:

receiving physiological data of the measured physiological parameters from the sensor devices over the MBAN; and, relaying the received physiological data to a patient monitoring system over a second communication network which analyzes the physiological data in real-time.

14. At least one controller configured to perform the method according to claim 10.

15. A candidate coordinator comprising:

a controller configured to:

receive a coordinator switching inquiry from a controller of a medical body area network (MBAN), the coordinator associated with one or more devices of the MBAN;

transmitting a switch inquiry request for one of the identified candidate coordinators to replace the coordinator on each channel for which the coordinator is authorized to operate on receiving the switch inquiry responses from at least one of the candidate coordinators on the channels for which the coordinator is authorized to operate on for a predetermined time interval;

transmit a response to the coordinator switching inquiry indicating a willingness to replace the coordinator to the coordinator;

receive a request to replace the coordinator, the request identifying the devices;

allocate resources for the identified devices;

transmit a response accepting the request to the coordinator, the response including data identifying the allocated resources for the devices; and receive data from the devices using the allocated resources;

wherein the switch inquiry requests include data identifying the number of devices associated with the coordinator and authentication data which includes at least one of a patient identifier and a service identifier.

16. The candidate coordinator according to claim 15, wherein the devices are sensor devices measuring physiological parameters of a patient.

17. The candidate coordinator according to claim 16, wherein the controller is further configured to:

receive physiological data of the measured physiological parameters from the sensor devices over the MBAN; and, relay the received physiological data to a patient monitoring system over a second communication network which analyzes the physiological data in real-time.

18. A Medical Body Area Network (MBAN) medical system, comprising:

at least one sensor device configured to measure at least one physiological parameter of a patient;

a patient monitor system;

a communication network configured to connect the at least one sensor device and the patient monitor system;

the candidate coordinator according to claim 15.

* * * * *